US012797046B2

(12) United States Patent
Zheng et al.

(10) Patent No.: US 12,797,046 B2
(45) Date of Patent: Nov. 17, 2026

(54) METHOD AND SYSTEM FOR EXPANDING FUNCTION OF ULTRASONIC IMAGING DEVICE

(71) Applicant: EIELING TECHNOLOGY LIMITED, Hong Kong (HK)

(72) Inventors: Yongping Zheng, Hong Kong (HK); Zihao Huang, Hong Kong (HK); Lok Kan Cheng, Hong Kong (HK); Like Wang, Hong Kong (HK)

(73) Assignee: EIELING TECHNOLOGY LIMITED, Hong Kong (HK)

( * ) Notice: Subject to any disclaimer, the term of this patent is extended or adjusted under 35 U.S.C. 154(b) by 421 days.

(21) Appl. No.: 18/572,162

(22) PCT Filed: Sep. 23, 2022

(86) PCT No.: PCT/CN2022/121032
§ 371 (c)(1),
(2) Date: Dec. 19, 2023

(87) PCT Pub. No.: WO2023/165119
PCT Pub. Date: Sep. 7, 2023

(65) Prior Publication Data

US 2024/0115245 A1 Apr. 11, 2024

(30) Foreign Application Priority Data

Mar. 3, 2022 (CN) ........................ 202210203574.3

(51) Int. Cl.
*A61B 8/00* (2006.01)

(52) U.S. Cl.
CPC ................ *A61B 8/54* (2013.01); *A61B 8/462* (2013.01); *A61B 8/465* (2013.01); *A61B 8/523* (2013.01); *A61B 8/565* (2013.01)

(58) Field of Classification Search
CPC ........... A61B 8/54; A61B 8/462; A61B 8/465; A61B 8/523; A61B 8/565
See application file for complete search history.

(56) References Cited

U.S. PATENT DOCUMENTS 5,603,323 A 2/1997 Pflugrath et al.
6,547,730 B1 * 4/2003 Lin ..................... A61B 8/4411 600/437

(Continued)

FOREIGN PATENT DOCUMENTS

CN 107661121 A 2/2018
CN 111281422 A 6/2020

(Continued)

OTHER PUBLICATIONS

International Search Report of PCT Patent Application No. PCT/CN2022/121032 issued on Dec. 15, 2022.

(Continued)

*Primary Examiner* — Tadesse Hailu

(57) ABSTRACT

A method for expanding functions of an ultrasonic imaging device, comprising: identifying and comparing functions of an integrated imaging device and a to-be-expanded ultrasonic imaging device; on the basis of a comparison result, configuring operating parameters and modes of the integrated imaging device and the to-be-expanded ultrasonic imaging device which serves as a host machine; enabling the integrated imaging device to be in communication with the host machine; and operating the integrated imaging device and displaying ultrasound data by means of a user terminal of the host machine. There is no need to make any changes to the hardware of the existing host machine, and new functions can be integrated into the existing device only by upgrading or making minor modifications to the software, such that a new application is derived from a traditional ultrasonic imaging device.

20 Claims, 5 Drawing Sheets

(56) References Cited

U.S. PATENT DOCUMENTS

| | | | | |
|---|---|---|---|---|
| 6,783,493 | B2 * | 8/2004 | Chiang ............... | G01S 7/52074 600/437 |
| 2004/0015079 | A1 * | 1/2004 | Berger .................. | G01S 7/5208 600/443 |
| 2008/0194951 | A1 | 8/2008 | Poland | |
| 2011/0263983 | A1 * | 10/2011 | Peszynski .............. | A61B 8/445 600/443 |
| 2012/0041313 | A1 * | 2/2012 | Tanaka ................... | A61B 8/065 600/443 |
| 2013/0226001 | A1 | 8/2013 | Steen et al. | |
| 2014/0051984 | A1 * | 2/2014 | Berger ................... | A61B 18/02 600/424 |
| 2016/0015368 | A1 | 1/2016 | Poland | |
| 2016/0278739 | A1 * | 9/2016 | Pelissier ................ | A61B 8/465 |
| 2019/0043387 | A1 * | 2/2019 | Dickie ................. | G09B 23/286 |
| 2019/0099155 | A1 * | 4/2019 | Notohara ........... | A61B 17/3403 |
| 2021/0052256 | A1 * | 2/2021 | Berger ................. | A61B 8/4455 |
| 2023/0204742 | A1 * | 6/2023 | Haque ................. | G01S 15/8915 367/7 |

FOREIGN PATENT DOCUMENTS

| | | | |
|---|---|---|---|
| CN | 111789633 | A | 10/2020 |
| CN | 112336373 | A | 2/2021 |
| CN | 113855072 | A | 12/2021 |
| CN | 114052780 | A | 2/2022 |

OTHER PUBLICATIONS

European Search Report of European Patent Application No. 22929549.8 issued on Dec. 18, 2025.

* cited by examiner

METHOD AND SYSTEM FOR EXPANDING FUNCTION OF ULTRASONIC IMAGING DEVICE

TECHNICAL FIELD

The present application relates to the field of ultrasound imaging, more specifically, it relates to a method for expanding functions of ultrasonic imaging devices and a functionally expandable ultrasound imaging system.

BACKGROUND

Ultrasound applications for diagnostic purposes include structural imaging and functional imaging, which are used to visualize the anatomical structure of the object under test and to measure the physiological function of the object under test, respectively. Conventional ultrasound imaging technology is widely used in medical practice and serves ultrasound examinations with some fixed classical functions. Due to reasons such as fierce market competition and high capital investment, devices with traditional functions are mainly produced and dominated by large-scale manufacturers in order to gain a higher market share. From another perspective, the application areas of the ultrasound industry are relatively independent, and the functions configured depend on the manufacturer to which they belong. Due to differences in technical barriers, intellectual property ownership, patent protection, talent pool and development philosophy, it is almost impossible to integrate the use of ultrasound device produced by different manufacturers in the market.

However, with newer concepts and technological advances, application-oriented or disease-oriented ultrasound technology is in the midst of a boom and continues to expand the ultrasound industry's footprint. As a result, a number of startups and small businesses have taken over areas that were traditionally inaccessible to the big ultrasound players through innovative technologies. Specific examples include: liver fibrosis detection based on transient elastometry, cerebrovascular detection based on transcranial ultrasound Doppler, scoliosis detection based on 3D imaging, carotid atherosclerosis detection based on 3D imaging, and fetal prenatal detection based on 4D imaging. The above functions are mainly realized by respective independent and application-specific ultrasound systems.

A conventional ultrasonic imaging system usually consists of three parts: an ultrasound probe, a host machine, and a display unit. Typically, the probe includes a piezoelectric transducer for scanning the object under test, the host machine includes front-end hardware circuitry and a computer for controlling and processing the ultrasound data, and the display unit is used for interacting with the user. Typically, a single system provides several standard probe interfaces for converting and configuring different probes. Specifically, a "probe" in the narrow sense is used only to emit ultrasound and receive an echo signal. The probes are configured on their own ultrasound system by means of probe interfaces in the front-end hardware circuitry, and are connected to their own system via cable connections for the transmission of data and information. Each probe has a specific imaging purpose and is used to perform a specific function. If a new probe is to be configured on an existing device, conventional integration methods have the disadvantages of being costly, laborious, technically complex, and difficult to operate. At the hardware level, the integration work involves altering the front-end circuitry of the existing device and the probe interface based on the front-end hardware circuitry; at the software level, the integration work requires access to source code and control. As a result, the conventional configuration scheme described above suffers from the following drawbacks: first, the interface wiring sequences of the probes may be defined differently by each manufacturer and are poorly compatible, resulting in the probes being constructed to function only for the system to which they belong; second, when a new probe used to carry out a particular function is configured on an existing device that does not support the application, the function may not be realized. Specifically, at the software level, the existing device may not be able to display a particular user interface and lack corresponding processing algorithms; at the hardware level, the existing device may lack the circuitry and communication interfaces for controlling the various components within the probe; and thirdly, it is costly to modify the front-end hardware circuits and the probe interfaces within the existing device in order to configure the new probe.

It is expected that many new features will be added to existing devices at no additional cost. From the user's point of view, the addition of new features can satisfy more diagnostic needs and explore more ultrasound applications; from the point of view of large vendors, the addition of new features can increase the competitiveness of their existing devices; from the point of view of developers focusing on a specific application, parasitizing a new feature onto an existing device can increase the accessibility and popularity of the feature, which is conducive to enhancing market penetration.

In summary, how to integrate specific ultrasound functions into traditional ultrasonic imaging devices that are not originally compatible with such functions, and expand the application range of existing devices, is an urgent problem for practitioners in the ultrasound industry.

SUMMARY

The present application provides a method for expanding functions of an ultrasonic imaging device, comprises the following steps:

- S1. identifying and comparing functions of an integrated imaging device and a to-be-expanded ultrasonic imaging device;
- S2. on the basis of a comparison result, configuring operating parameters and modes of the integrated imaging device and the to-be-expanded ultrasonic imaging device which serves as a host machine;
- S3. enabling the integrated imaging device to be in communication with the host machine;
- S4. operating the integrated imaging device and displaying ultrasound data by means of a user terminal of the host machine.

In the method for expanding functions of an ultrasonic imaging device provided by the present application, in the step S1, the functions of the integrated imaging device and the to-be-expanded ultrasonic imaging device is identified based on user's inputs to the integrated imaging device, user's inputs to the host machine, and/or sensing information from at least one sensor.

In the method for expanding functions of an ultrasonic imaging device provided by the present application, in the step S2, if the comparison result indicates that the function of the integrated imaging device is not compatible with the function supported by the to-be-expanded ultrasonic imaging device, configuring the host machine by importing packaged executable program code to the host machine.

In the method for expanding functions of an ultrasonic imaging device provided by the present application, the ultrasound data includes ultrasound images, videos, and measurement values that have been processed through signal and/or image processing techniques.

In the method for expanding functions of an ultrasonic imaging device provided by the present application, the integrated imaging device is connected to a universal interface of the host machine.

In the method for expanding functions of an ultrasonic imaging device provided by the present application, the step S4 comprises:

S41. transferring the ultrasound data obtained by the integrated imaging device to a cloud server;

S42. performing signal processing, image processing, image reconstruction, and/or multidimensional visualization on the ultrasound data on the cloud server;

S43. transmitting the processed ultrasound data to the user terminal for display.

In the method for expanding functions of an ultrasonic imaging device provided by the present application, the step S4 comprises:

S41'. acquiring and processing the ultrasound data through the integrated imaging device;

S42'. transmitting the processed ultrasound data to the user terminal for display via the universal interface of the host machine.

The present application further provides a functionally expandable ultrasonic imaging system, comprises an integrated imaging device and a host machine of a to-be-expanded ultrasonic imaging device, the integrated imaging device comprises:

an imaging device, used to scan an object under test and process corresponding ultrasound data;

an integrated imaging device communication interface, used to establish a communication connection with the host machine, enabling bidirectional data transmission between the integrated imaging device and the host machine;

an integrator, used to identify and compare functions of the integrated imaging device and the host machine, and on the basis of a comparison result, configure operating parameters and modes of the integrated imaging device and a host machine;

the host machine comprises:

a user terminal, used to operate the integrated imaging device and display the ultrasound data;

a host machine communication interface, used to establish a communication connection with the integrated imaging device, enabling bidirectional data transmission between the integrated imaging device and the host machine.

In the functionally expandable ultrasonic imaging system provided by the present application, the host machine communication interface is a universal interface of the host machine.

In the functionally expandable ultrasonic imaging system provided by the present application, the ultrasound data includes ultrasound images, videos, and measurement values that have been processed through signal and/or image processing techniques.

In the functionally expandable ultrasonic imaging system provided by the present application, the functions of the integrated imaging device and the to-be-expanded ultrasonic imaging device is identified by the integrator based on user's inputs to the integrated imaging device, user's inputs to the host machine, and/or sensing information from at least one sensor.

In the functionally expandable ultrasonic imaging system provided by the present application, if the comparison result indicates that the function of the integrated imaging device is not compatible with the function supported by the to-be-expanded ultrasonic imaging device, packaged executable program code is imported to the host machine by the integrator to configure the host machine.

In the functionally expandable ultrasonic imaging system provided by the present application, the integrated imaging device is used for at least one of the following applications: one-dimensional imaging, two-dimensional imaging, three-dimensional imaging, four-dimensional imaging, elastography, elasticity measurement, viscoelasticity imaging, blood flow imaging, acoustic attenuation imaging, and ultra-high-speed ultrasound imaging.

In the functionally expandable ultrasonic imaging system provided by the present application, the communication connection between the integrated imaging device communication interface and the host machine communication interface can be either wireless or wired.

In the functionally expandable ultrasonic imaging system provided by the present application, the integrated imaging device also includes at least one sensor that is used to perceive operational status information of the integrated imaging device, and based on the operational status information, facilitate pairing and integration between the integrated imaging device and the host machine.

In the functionally expandable ultrasonic imaging system provided by the present application, signal processing, image processing, and image reconstruction on the images are performed by the imaging device.

In the functionally expandable ultrasonic imaging system provided by the present application, further comprises a cloud server, used to perform at least one of the following functions: the signal processing, image processing, image reconstruction, and/or multidimensional display.

In the functionally expandable ultrasonic imaging system provided by the present application, the cloud server is wirelessly connected to the integrated imaging device.

In the functionally expandable ultrasonic imaging system provided by the present application, the cloud server is wirelessly connected to the host machine.

In the functionally expandable ultrasonic imaging system provided by the present application, the integrated imaging device includes a user interface that is used to receive user's inputs and/or implement certain functions of the user terminal in the host machine.

In the functionally expandable ultrasonic imaging system provided by the present application, the imaging device can be an ultrasonic imaging device, an optoacoustic imaging device, or a thermoacoustic imaging device.

The implement of the method for expanding functions of an ultrasonic imaging device and the functionally expandable ultrasonic imaging system of the present application may achieve at least the following beneficial effects: utilizing software and hardware resources of an existing ultrasonic imaging device, on the basis of the functions of the integrated imaging device and the host machine, the integrated imaging device and the host machine are integrated for expanding functions of an existing device. There is no need to make any changes to the hardware of the existing host machine, and new functions can be integrated into the existing device only by upgrading or making minor modifications to the software, such that a new application is derived from a traditional ultrasonic imaging device.

DESCRIPTION OF THE DRAWINGS

In order to more clearly illustrate the technical solutions in the embodiments of the application or the prior art, the accompanying drawings to be used in the description of the embodiments or the prior art will be briefly introduced below, and it will be obvious that the accompanying drawings in the following description are only embodiments of the application, and that other accompanying drawings can be obtained according to the provided drawings for a person of ordinary skill in the field without putting forth creative labor.

DETAILED DESCRIPTION OF THE PREFERRED EMBODIMENT

The inventive concept of the present application is to utilize a general computer interface and display unit within an existing device, integrate an application-specific integrated imaging device with an existing ultrasonic imaging device, build a compatible ultrasonic imaging system at the software level, and expand the functions of the existing device. The integrated imaging device has a complete hardware system, eliminating the need to utilize existing device to participate in the realization of functions at the hardware level, including control scheduling and data processing. Upon integration, the integrated imaging device becomes one of the external devices of the computer within the existing device. The display unit within the existing device becomes one of the user terminals of the integrated imaging device. It is further contemplated in the present application to utilize the common computer interface and the display unit within the existing device to integrate the integrated imaging device based on other imaging means such as photoacoustic imaging or thermoacoustic imaging and the existing ultrasonic imaging device to build a compatible biomedical imaging system at the software level. Further, all or part of the work of the processing unit within the integrated imaging device or the computer within the existing device is handed over to a cloud server for execution, and the data is analyzed and processed in the cloud. This method eliminates the need for the existing device to be involved in data processing.

The First Embodiment

Figure 1:
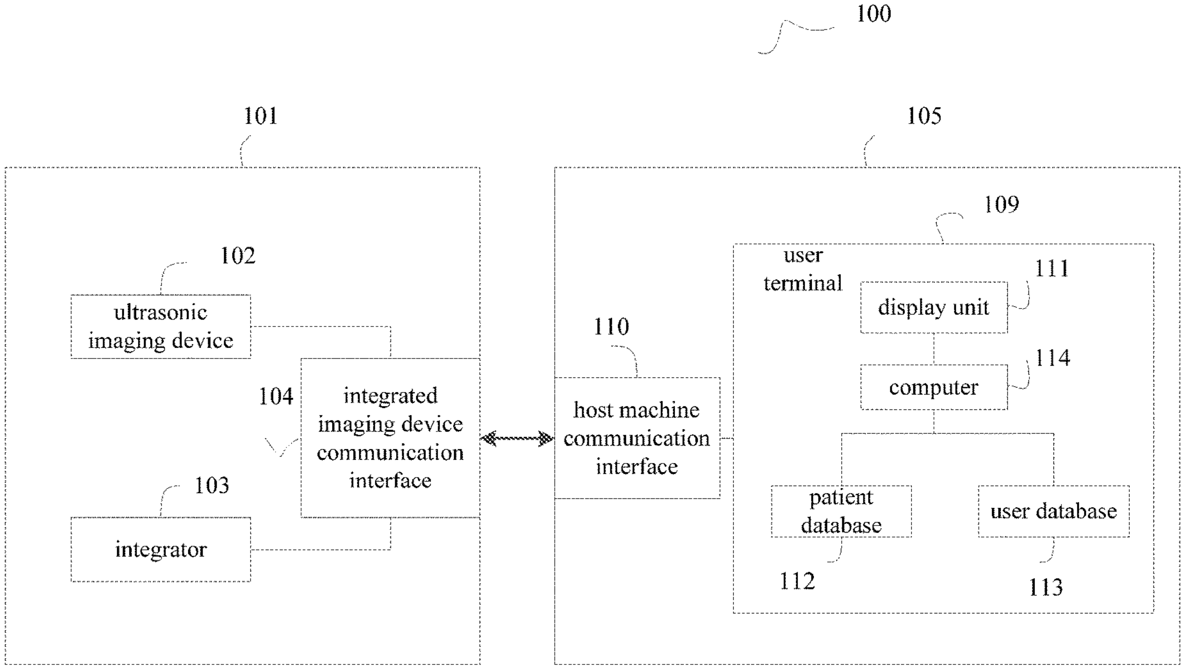
FIG. 1 shows a schematic diagram of a functionally expandable ultrasonic imaging system provided in the first embodiment of the present application.

A block diagram of a functionally expandable ultrasonic imaging system is shown in FIG. 1.

Referring to FIG. 1, the present embodiment provides an functionally expandable ultrasonic imaging system. The system 100 comprises an integrated imaging device 101 and a host machine 105. It should be known to those skilled in the art that said integrated imaging device 101 has a complete hardware system that can independently run the configured ultrasound imaging functions, and mainly comprises an ultrasonic imaging device 102, an integrator 103, and an integrated imaging device communication interface 104; and that the host machine 105 is a part of an existing ultrasonic imaging device, mainly comprising a user terminal 109 and a host machine communication interface 110. The integrated imaging device 101 and the host machine 105 are identified and compared in function by the integrator 103, and based on the comparison results, operating parameters and modes of the integrated imaging device and the host machine are configured. When the integration is completed, the ultrasound data obtained from the scanning of the ultrasonic imaging device 102 is transmitted to a user terminal for display through the integrated imaging device communication interface and the host machine communication interface. At the same time, the user can operate the integrated imaging device through the user terminal. Thus, within the system 100, the integrated imaging device 101 becomes an external device of the computer within the host machine 105. At the same time, the user terminal 109 of the host machine 105 becomes a terminal device of the integrated imaging device 101.

In this embodiment, said ultrasonic imaging device 102 comprises an ultrasound transducer, a control unit, a processing unit and a storage unit for performing an ultrasound scan of an object under test and generating ultrasound data of the object under test for carrying out a specific imaging application. A one-dimensional ultrasound image (e.g., an A-image and an M-image), a two-dimensional ultrasound image (e.g., a B-image, a Doppler image, an elasticity image), a three-dimensional ultrasound image, or a four-dimensional ultrasound image may be generated by the ultrasonic imaging device 102.

Specifically, the ultrasound transducer comprises a single transducer array element arranged in points or by several transducer array elements arranged in a line array, a convex array, or a two-dimensional matrix for emitting ultrasound waves to the object under test and receiving an echo signal. Non-limiting transducer elements include piezoelectric elements, MEMS elements, or other transducer elements. A control unit is used to coordinate the functions of the units or components for executing commands to control probe operation. The processing unit is used to process ultrasound data to construct an ultrasound image, including an A-mode image, an M-mode image, a B-mode image, a Doppler image, an elastic image, a three-dimensional image, or a four-dimensional image. The storage unit is based on at least one of the hardware or the software and contains executable program code driving the integrated imaging device 101 for caching and packaging the data. Said data is data related to ultrasound and/or other information including, but not limited to: imaging data, transducer configuration data, other transducer data, a user database from a host machine and a patient database. It is noted that the processing unit and the storage unit may be built into the integrated imaging device 101. In another embodiment, the setup of the processing unit and the storage unit is not limited to the integrated imaging device 101, but may also be set up in the host machine 105 (described below). The processing unit and the storage unit are at least part of the host machine 105 and all or part of their functions are performed by the host machine 105. The person skilled in the art should be aware that said integrated imaging device 101 is based on the ultrasonic imaging device 102 and uses other imaging means or sets up other sensors and components to realize specific functions. Non-limitingly, said integrated imaging device 101 is application-specific for carrying out at least one of a one-dimensional imaging application, a two-dimensional imaging application, a three-dimensional imaging application, and a four-dimensional imaging, elastography, elastometry, viscoelasticity imaging, hemodynamic imaging, acoustic attenuation imaging, and ultrahigh-speed ultrasound imaging application; it may be a low-frequency vibration-based transient elasticity measurement device (with elasticity measurement function), an ultrasound imprinting elasticity measurement device (with elasticity measurement capabilities), shear wave elasticity imaging device based on acoustic radiation force pulses (with elasticity imaging and measurement capabilities), strain elasticity imaging device based on quasi-static forces (with elasticity imaging and measurement capabilities), spatial transducer-based three-dimensional ultrasonic imaging device (with three-dimensional imaging capabilities), and transcranial ultrasound Doppler device (with blood flow measurement capabilities), intravascular ultrasonic imaging device (having vascular imaging function), ultrasound endoscopy device (having gastrointestinal tract imaging function), ultrasound tomography device (having tomographic and three-dimensional imaging function), and the like. It is worth noting that the present application does not limit the shape, frequency, communication interface type, imaging mode, operation mode, application and function of the integrated imaging device. The integrated imaging device in this embodiment may carry out any of the functions and applications known in the art.

In this embodiment, the integrator 103 is used to integrate the integrated imaging device 101 into the host machine 105 at the software level, and does not involve integration at the hardware circuit level, allowing said integrated imaging device 101 to be used with any host machine. It should be understood that if the integrator 103 is not working, the integrated imaging device 101 can only be used with a host machine 105 that supports the function or application of the integrated imaging device 101. The integrator 103 has the following functions: 1) identifying the functions of the integrated imaging device 101 and the functions supported/compatible by the host machine 105 and comparing them; 2) based on the comparison results of the functions of the integrated imaging device 101 and the host machine 105, configuring the operating parameters and modes within the integrated imaging device 101 that satisfy the requirements for operating on the host machine 105; 3) based on the pairing results of the integrated imaging device 101 and the host machine 105, if the host machine 105 does not support/is not compatible with the functions of said integrated imaging device 101, configuring the operating parameters and modes within the host machine 105 that satisfy working on the integrated imaging device 101 by importing the packaged executable program code (including the front-end user interface code and the back-end processing algorithm) into the host machine 105, so as to realize the integrated imaging device 101 to be integrated with the host machine 105 at a software level. Wherein, the application modes include, but are not limited to: a one-dimensional application, a two-dimensional application, a three-dimensional application, and a four-dimensional application, etc.; and the operation modes include, but are not limited to: an ultrasonography mode, an elasticity measurement mode, an elasticity imaging mode, a viscoelasticity imaging mode, an acoustic attenuation imaging, an ultrahigh-speed ultrasound imaging, a blood flow measurement mode, a vascular imaging mode, a gastrointestinal tract imaging mode, a spine three-dimensional reconstruction mode, and a muscle three-dimensional reconstruction mode, Vascular Reconstruction Mode. The specific modes depend on the functions and applications supported by the integrated imaging device and are not limited by the present application.

In this embodiment, the integrated imaging device communication interface 104 is constructed on the integrated imaging device 101 for communicatively connecting with the host machine 105 to realize bidirectional data transmission between the integrated imaging device 101 and the host machine 105. The communication connection includes a wireless connection and a wired connection. The wired communication protocols include, but are not limited to: universal serial bus (USB), serial peripheral interface (SPI), Thunderbolt, PCIe, integrated circuit bus (I2C). Wireless communication protocols include, but are not limited to: WiFi, Bluetooth, Ultra-Wide Bandwidth (UWB), ZigBee, Radio Frequency Identification (RFID), Near Field Communication (NFC), 4G technology, or 5G technology. It should be appreciated by those skilled in the art that said integrated imaging device communication interface 104 is constructed to have a single or multiple communication interfaces for communicating and connecting with a host machine 105 that supports different communication protocols and interface types.

In this embodiment, said host machine 105 comprises a user terminal 109 and a host machine communication interface 110. Said user terminal 109 is at least a part of the host machine 105 that has been configured with a computer for at least one of displaying ultrasound images, displaying ultrasound-related data, controlling the operation of the integrated imaging device, and managing the database and post-processing data. Specifically, said user terminal 109 comprises a display unit 111, a patient database 112, a user database 113 and a computer 114. As far as the display function is concerned, the user terminal 109 is used only for displaying ultrasound data in picture and/or video format, but is not related to data processing. Said user terminal 109 is using the existing display unit 111 on the host machine as the terminal platform for interacting with the user without any changes to the host machine at the hardware level, and belongs to one of the parts of the firmware of the computer within the host machine. Said display unit 111 may be an external display device or a cathode ray tube display or an LCD screen embedded in the ultrasonic imaging device for displaying ultrasound images, measurements and/or ultrasound data obtained by the integrated imaging device. The form of the display depends on the existing setup of the host machine. Secondly, as far as the operation control function is concerned, when the integrated imaging device 101 is integrated into the host machine 105 at the software level, the user terminal 109 is used to host packaged executable program code (including front-end user interface code and back-end processing algorithms). It is worth stating that the user interface and processing algorithms are constructed to be compatible with said host machine 105. The form of user interaction depends on the existing setup of the host machine. Thirdly, as far as data management is concerned, the user has access to the patient database 112 and the user database 113 of said integrated imaging device 101 under the current application. fourthly, as far as data processing functions are concerned, the computer 114 within said host machine stores various algorithms for accomplishing all or part of the work of the processing unit 106 within the integrated imaging device 101. This approach saves resources and arithmetic power of the integrated imaging device 101. Optionally, the user terminal 109 is involved in signal processing, image processing, image reconstruction or multidimensional display, which may be applicable to the following three situations: 1) complete processing of data that has not been processed by the integrated imaging device 101; 2) further processing of data that has been pre-processed by the integrated imaging device 101; and 3) post-processing of data that has been processed by the integrated imaging device 101.

In this embodiment, said host machine communication interface 110 is at least a portion of the host machine 105 that has been configured with a computer, and belongs to a generic computer interface within the host machine 105. Said host machine communication interface 110 is constructed on a computer of the host machine 105 for communicating and connecting with the integrated imaging device 101 to realize bi-directional data transfer between the integrated imaging device 101 and the host machine 105. It is noted that the successful pairing of the integrated imaging device 101 with the host machine 105 depends on the type of interface of the existing host machine communication interface 110. Preferably, said host machine communication interface 110 is existing and does not require any changes to the host machine and is part of the firmware of one of the computers within the host machine. In another embodiment, if the integrated imaging device communication interface 104 is physically incompatible with the host machine communication interface 110, only a suitable adapter for the host machine communication interface 110 needs to be configured, and a communication connection can be established by making minor changes at the hardware level. For example, when the host machine communication interface 110 only supports the USB communication protocol, configuring a USB-WiFi adapter on the USB interface may enable the host machine to realize a paired connection with an integrated imaging device that supports the WiFi communication protocol.

Figure 2:
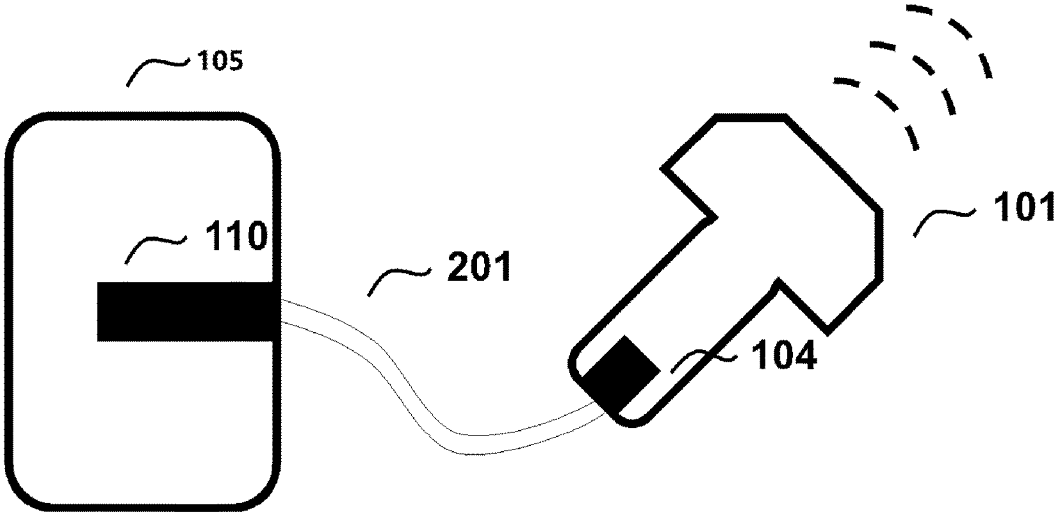
FIG. 2 shows a schematic diagram of a three-dimensional structure of a functionally expandable ultrasonic imaging system provided in the first embodiment of the present application.

FIG. 2 is a schematic diagram of a three-dimensional structure of a system based on a wired communication protocol provided in the first embodiment of the present application.

As shown in FIG. 2, a pluggable cable connection 201 is used between the integrated imaging device communication interface 104 and the host machine communication interface 110. Data transmission between the integrated imaging device 101 and the host machine 105 is via a wired communication protocol. The wired communication protocols include, but are not limited to: universal serial bus (USB), serial peripheral interface (SPI), Thunderbolt, PCIe, integrated circuit bus (I2C). As a result, the integrated imaging device is integrated at the software level into existing ultrasonic imaging devices as a sub-function to be used with existing devices that are otherwise incompatible or do not support the specific application.

The Second Embodiment

Figure 3:
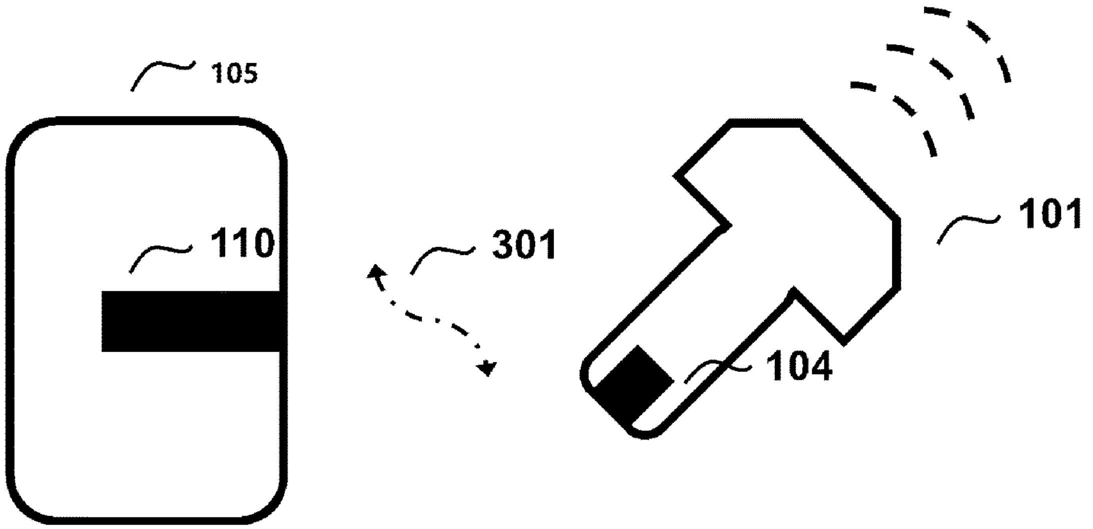
FIG. 3 is a schematic diagram of a three-dimensional structure of a functionally expandable ultrasonic imaging system provided in the second embodiment of the present application.

FIG. 3 is a schematic diagram of a three-dimensional structure of a system based on a wireless communication protocol provided in the second embodiment of the present application.

The present embodiment provides a system that differs from the first embodiment in that a wireless connection 301 is used between the integrated imaging device communication interface 104 and the host machine communication interface 110, as shown in FIG. 3. In this embodiment, the data transmission between the integrated imaging device 101 and the host machine 105 is performed via a wireless communication protocol. The wireless communication protocols include, but are not limited to, WiFi, Bluetooth, Ultra-Wide Bandwidth (UWB), ZigBee, Radio Frequency Identification (RFID), Near Field Communication (NFC), 4G technology, or 5G technology. As a result, the integrated imaging device is integrated at the software level into existing ultrasonic imaging devices as a sub-function to be used with existing devices that are otherwise incompatible or do not support the specific application.

The Third Embodiment

Figure 4:
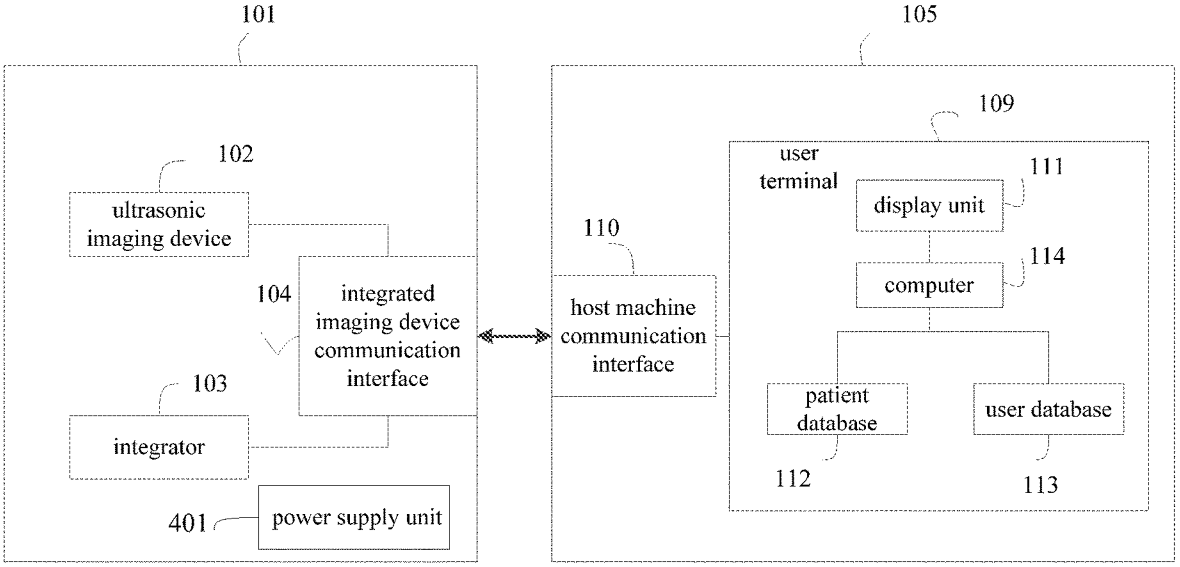
FIG. 4 is a schematic diagram of a functionally expandable ultrasonic imaging system provided in the third embodiment of the present application.

A block schematic diagram of a functionally expandable ultrasonic imaging system provided in the third embodiment is shown in FIG. 4.

The present embodiment provides a system that differs from the first embodiment in that further, the integrated imaging device 101 further comprises a power supply unit 401. Said power supply unit 401 contains a battery and associated circuitry for independently supplying power to the integrated imaging device 101. The charging method may be wireless charging or wired charging. In this embodiment, the integrated imaging device 101 does not need to rely on the host machine 105 to provide power, which is particularly suitable for the case of wireless connection.

The Fourth Embodiment

Figure 5:
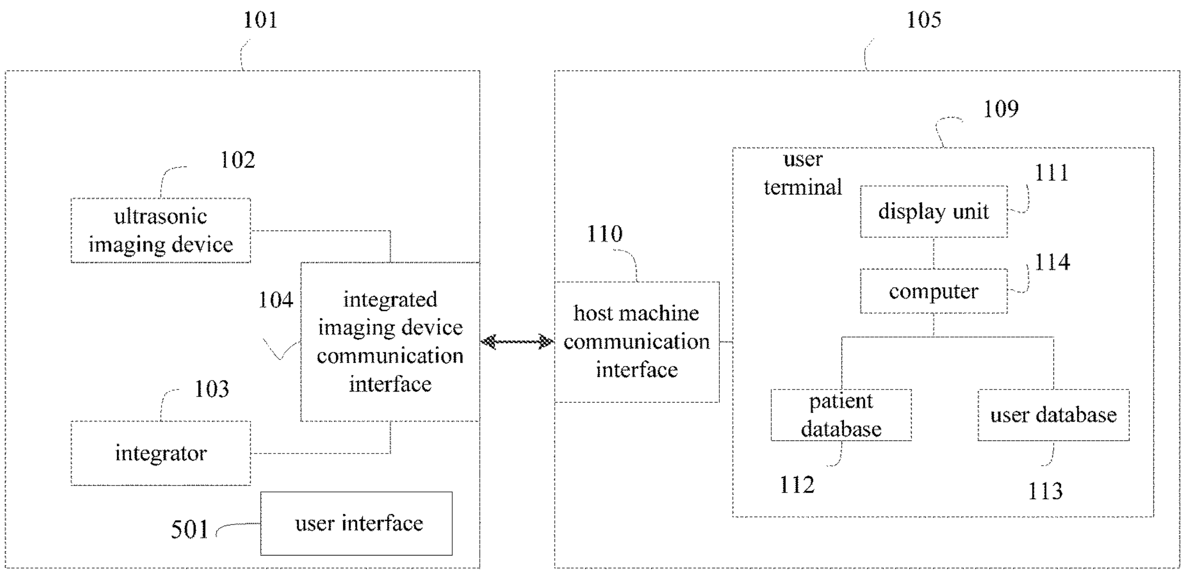
FIG. 5 is a schematic diagram of a functionally expandable ultrasonic imaging system provided in the fourth embodiment of the present application.

A block schematic diagram of a functionally expandable ultrasonic imaging system provided in the fourth embodiment is shown in FIG. 5.

The present embodiment provides a system that differs from the first embodiment in that further, the integrated imaging device 101 further comprises a user interface 501. Said user interface 501 is a hardware device that is physically disposed at any location of the integrated imaging device 101 for receiving commands entered by the user at the integrated imaging device side and based on the content of the commands in order to facilitate the pairing and integration of the integrated imaging device 101 and the host machine 105. Said commands include, but are not limited to, selection of an operation mode, selection of an application mode, adjustment of image parameters, and the like. The user input includes, but is not limited to: audio input, key manual input, touchpad manual input, touchscreen manual input. In another embodiment, the user interface 501 is used to realize part of the functions of the user terminal in the host machine, including displaying an ultrasound image (said user interface 501 is used to complete part of the work of the display unit 111), displaying ultrasound-related data (said user interface 501 is used to complete part of the work of the display unit 111), controlling the operation of the integrated imaging device (said user interface 501 is used to complete part of the work of the display unit 111 and the computer 114) and managing a database (said user interface 501 is used to complete part of the work of the patient database 112 and/or the user database 113).

The Fifth Embodiment

Figure 6:
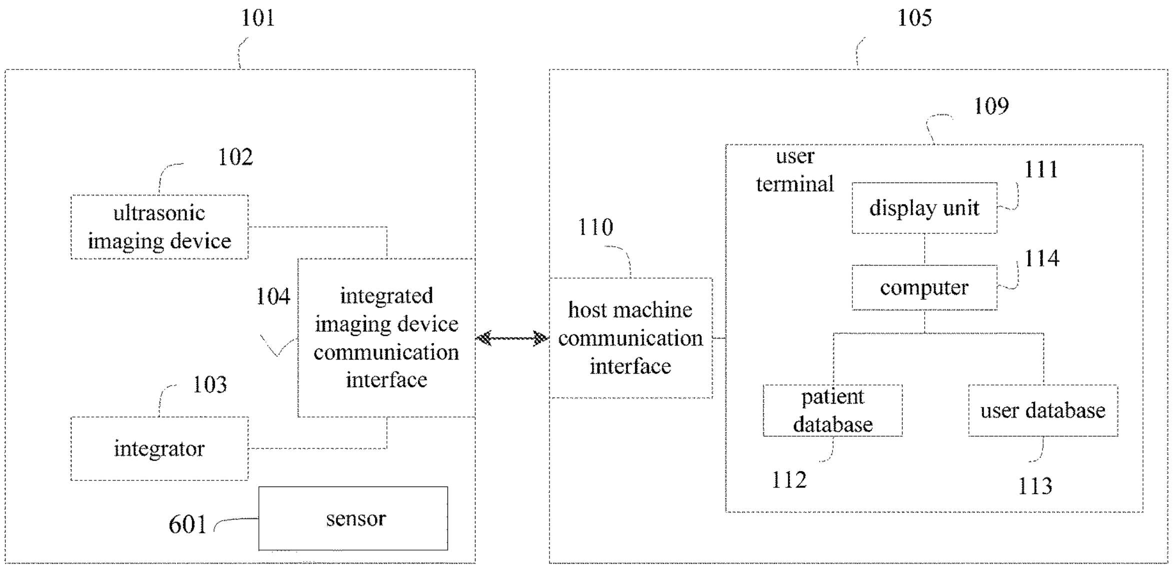
FIG. 6 is a schematic diagram of a functionally expandable ultrasonic imaging system provided in the fifth embodiment of the present application.

A block schematic diagram of a functionally expandable ultrasonic imaging system provided in the fifth embodiment is shown in FIG. 6.

The present embodiment provides a system that differs from the first embodiment in that further, the integrated imaging device 101 further comprises a sensor 601. Said sensor 601 may be at least one of a temperature sensor, a force sensor, a motion sensor, a three-dimensional spatial sensor, or a camera for sensing operational state information of the integrated imaging device 101 and based on the operational state information in order to facilitate the integrated imaging device 101 and the host machine 105 to pair and integrate. For example, if the integrated imaging device 101 has an application of three-dimensional imaging or four-dimensional imaging, the host machine 105 may analyze and pre-determine the application mode of said to-be-connected integrated imaging device 101 based on the data changes and operation information obtained by said three-dimensional spatial sensor 601; if the integrated imaging device 101 has an application of blood flow imaging, the host machine 105 may analyze and pre-determine the application mode of said to-be-connected integrated imaging device 101 based on the data changes and operation information obtained by said motion or force sensor 601. If the integrated imaging device 101 has the application of breast or liver elastography, the host machine 105 may analyze and predetermine the application mode of said to-be-connected integrated imaging device 101 based on the ultrasound image characteristics acquired by said integrated imaging device 101 combined with the operation information acquired by the force sensor 601. The operational status information sensed by the sensors may further facilitate the integration of the integrated imaging device and the host machine, thereby improving the pairing efficiency.

The Sixth Embodiment

Figure 7:
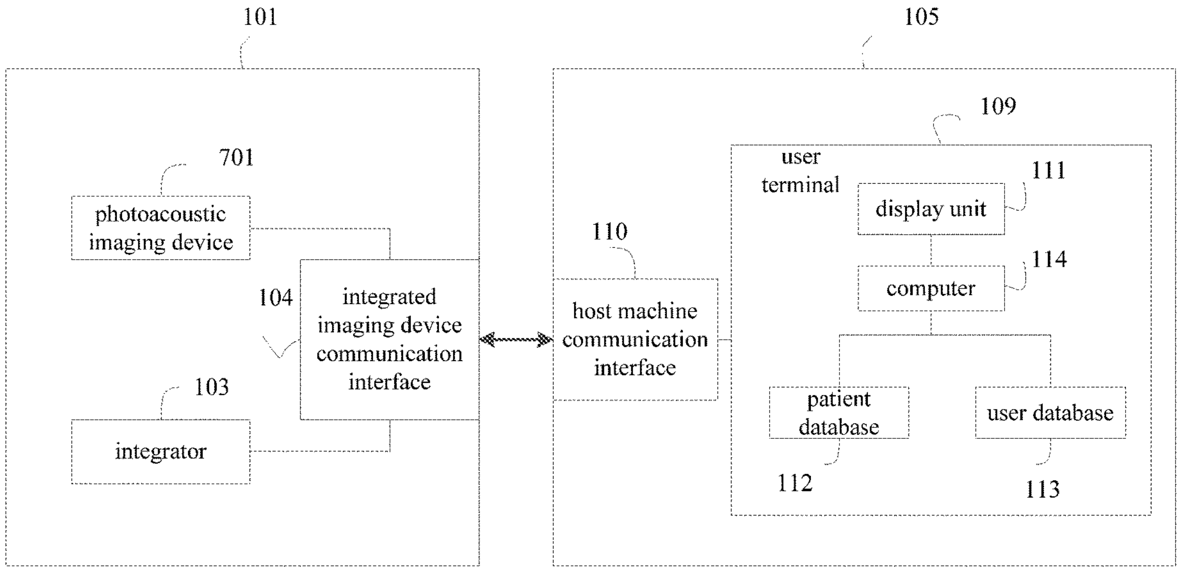
FIG. 7 is a schematic diagram of a functionally expandable ultrasonic imaging system provided in the sixth embodiment of the present application.

A block schematic diagram of a functionally expandable ultrasonic imaging system provided in the sixth embodiment is shown in FIG. 7.

The present embodiment provides a system that differs from the first embodiment in that the integrated imaging device 101 is not based on ultrasound imaging or the integrated imaging device 101 is not an application-specific ultrasound integrated imaging device, but is based on other biomedical imaging means such as photoacoustic imaging or thermoacoustic imaging. Said integrated imaging device 101 based on the photoacoustic imaging comprises a photoacoustic imaging device 701 for irradiating a pulsed laser to a subject and subsequently capturing the ultrasound signal generated by the light excitation of the tissue to generate a photoacoustic image. In another embodiment, said integrated imaging device 101 based on thermoacoustic imaging is used to irradiate a pulsed laser at a radio frequency to an object under test, and subsequently acquire ultrasound signals generated by light excitation of the tissue to generate a thermoacoustic image. Biomedical imaging means based on photoacoustic imaging or thermoacoustic imaging are developing rapidly, and the present application can integrate photoacoustic imaging and thermoacoustic imaging into an existing host by means of the integrated imaging device based on photoacoustic imaging or the integrated imaging device based on thermoacoustic imaging, thereby expanding the scope of use of photoacoustic and thermoacoustic imaging.

The Seventh Embodiment

Figure 8:
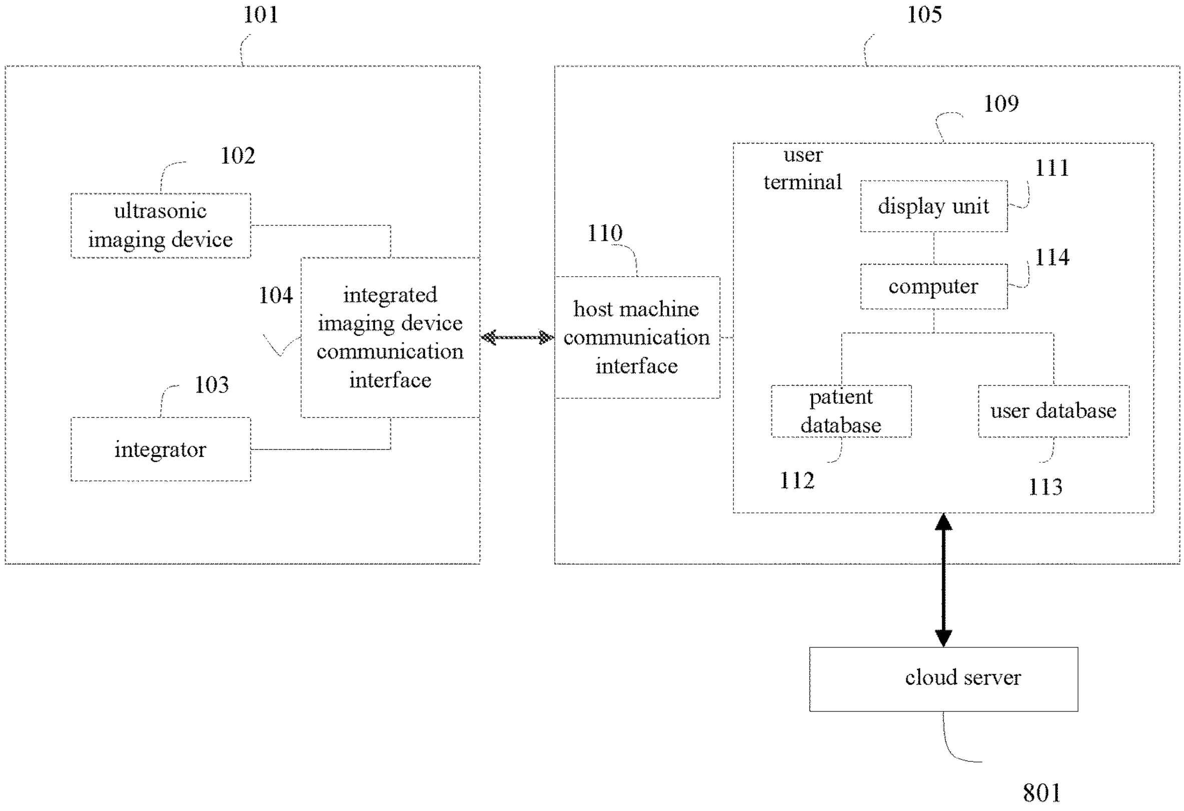
FIG. 8 is a schematic diagram of a functionally expandable ultrasonic imaging system provided in the seventh embodiment of the present application.

A block schematic diagram of a functionally expandable ultrasonic imaging system provided in the seventh embodiment is shown in FIG. 8.

The present embodiment provides a system that differs from the first embodiment in that further, the system 100 further comprises a cloud server 801. Said cloud server 801, is used to implement all or part of the functions of the user terminal 109 of the host machine 105 on the cloud. Said cloud server 801 is directly wirelessly connected to said host machine 105.

It should be appreciated by those skilled in the art that the system 100 is connected to the cloud server 801 via the host machine 105 by wired or wireless transmission and interoperates with the data. Specifically, the system 100 uploads the relevant data obtained by said integrated imaging device 101 to said cloud server 801 and similar processing modules via the user terminal 109; said cloud server 801 performs cloud computing on the data for analysis and processing. After analyzing, computing and processing in the cloud, the processed relevant data is transmitted back to the user terminal 109 for display.

It is worth stating that said cloud server 801 stores various algorithms and has a data processing function for realizing signal processing, image processing, image reconstruction or multidimensional display, which can be applied to the following three situations: 1) doing complete processing to the data that has not been processed by the local system 100; 1) doing further processing to the data that has been preprocessed by the local system 100; and 2) doing post-processing to the data that has already been processed by the local system 100. Preferably, a big data workstation may also be built on the cloud server for participating in data storage, management, retrospective analysis and sharing.

The Eighth Embodiment

Figure 9:
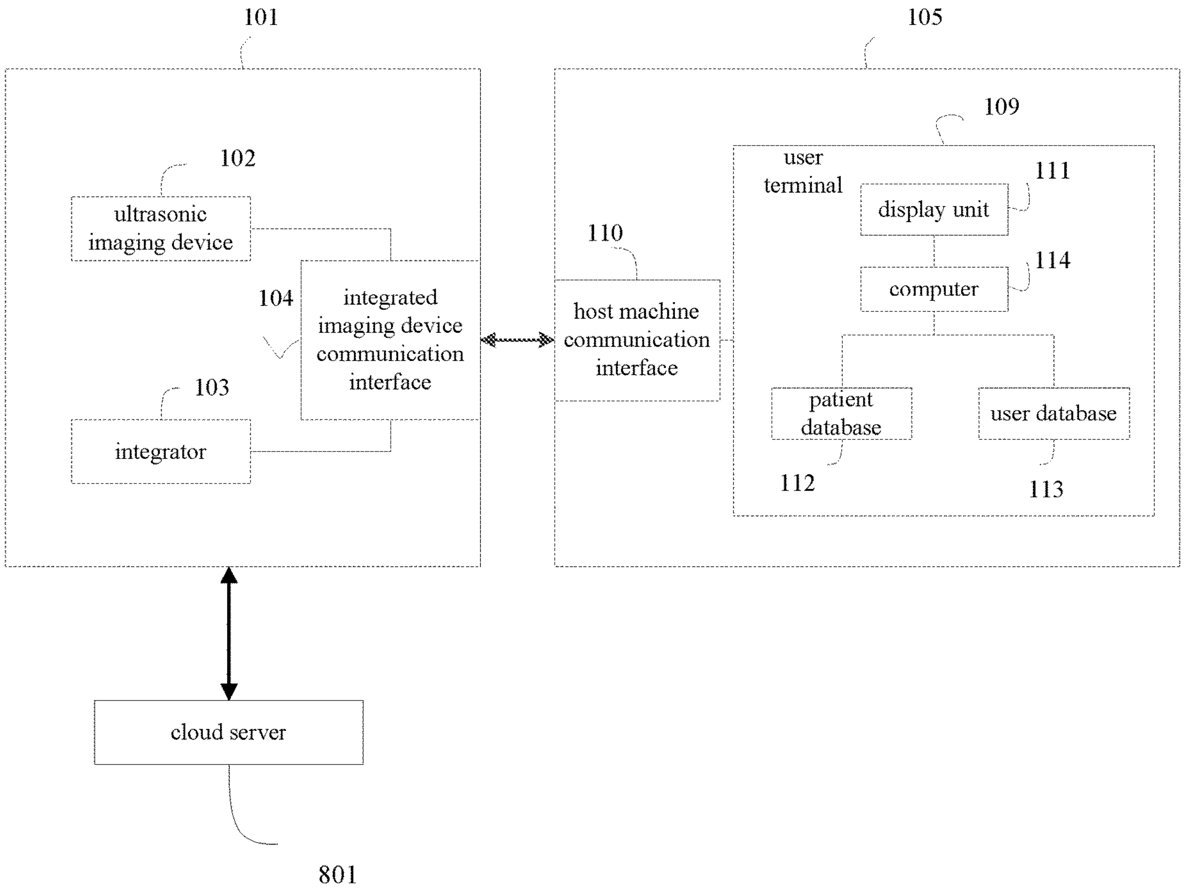
FIG. 9 is a schematic diagram of a functionally expandable ultrasonic imaging system provided in the eighth embodiment of the present application.

A block schematic diagram of a functionally expandable ultrasonic imaging system provided in the eighth embodiment is shown in FIG. 9.

The present embodiment provides a system that differs from the eighth embodiment in that said cloud server 801 is wirelessly connected directly to said integrated imaging device 101 without going through a host machine.

It should be appreciated by those skilled in the art that the system 100 is connected to the cloud server 801 via the integrated imaging device 101 by wired or wireless transmission and interoperates with the data. Specifically, the integrated imaging device 101 uploads relevant data obtained to said cloud server 801 and similar processing modules; said cloud server 801 performs cloud computing on the data for analysis and processing. After analyzing, computing and processing in the cloud, the processed relevant data is transmitted back to the integrated imaging device, which is then transmitted by the communication interface of the integrated imaging device to the user terminal of the host machine for display.

Using a cloud server 801 to interact with information from the integrated imaging device, this method does not require a host machine to participate in data processing, and has the following advantages: 1) saves the resources and arithmetic power of the local system; 2) promotes the miniaturization, integration, and portability of the hardware of the integrated imaging device; 3) facilitates the management of data; and 4) facilitates the updating, optimization, and execution of the more advanced AI-related algorithms.

The Ninth Embodiment

Figure 10:
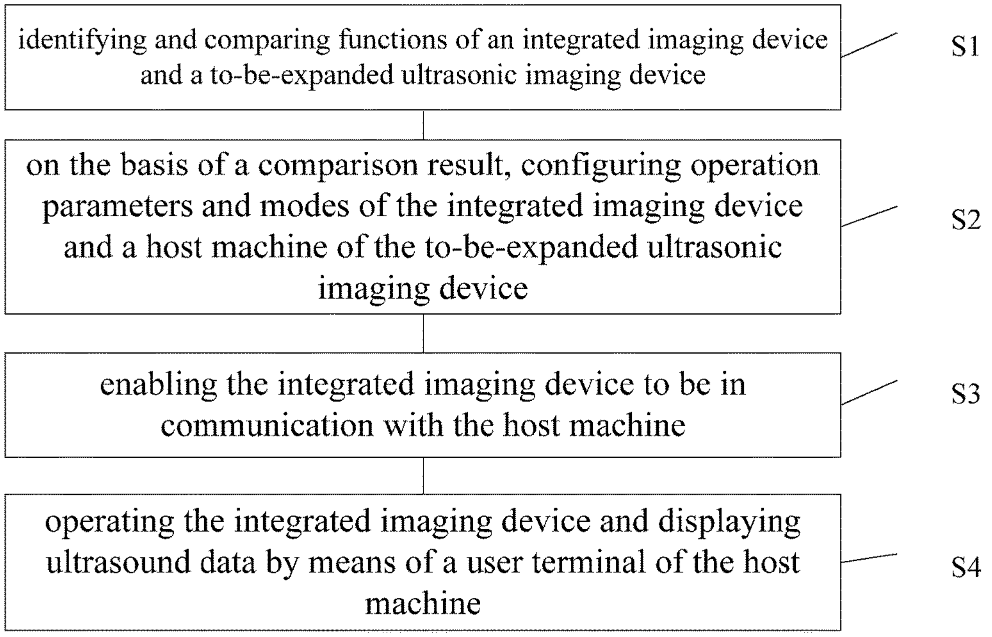
FIG. 10 shows a flowchart of steps of a method for expanding functions of an ultrasonic imaging device provided in ninth embodiment of the present application.

As shown in FIG. 10, the ninth embodiment provides a method for expanding the function of an ultrasonic imaging device, comprising the steps of:

S1, identify and compare the function of an integrated imaging device and a to-be-expanded ultrasonic imaging device;

Specifically, the way of recognizing the function of said integrated imaging device and the to-be-expanded ultrasonic imaging device comprises: based on the user's input to the integrated imaging device, based on the user's input to the host machine of the to-be-expanded ultrasonic imaging device and/or based on the sensing information of at least one sensor. Said integrated imaging device has a complete hardware system, which may be an application-specific integrated imaging device based on ultrasound imaging, or an integrated imaging device based on other biomedical imaging such as photoacoustic imaging or thermoacoustic imaging.

S2, based on the comparison results, configure the operating parameters and modes of said integrated imaging device and the to-be-expanded ultrasonic imaging device which serves as a host machine;

Specifically, if the result of the comparison is that the function of said integrated imaging device is incompatible with the function supported by the host machine, the integration is initiated by importing the packaged executable program code to the host machine to configure the host machine. If the result of the comparison is that the function of said integrated imaging device is compatible with the function supported by the host machine, the host machine has been configured with executable program code specific to said integrated imaging device. Based on the comparison results of the function of the integrated imaging device 101 and the host machine 105, the selected operation mode, the selected application mode, or user's inputs, the operating parameters and modes of the integrated imaging device and the host are configured, including, but not limited to, the type of communication interface, the imaging parameter, the measurement parameter, the imaging mode, the mode of operation, the application, and the function.

The configuration process includes: identifying the type and/or supported communication protocol of the integrated imaging device communication interface of said integrated imaging device, identifying the type and/or supported communication protocol of host machine communication interface of said host machine, setting the integrated imaging device to a standby connection state, importing packaged executable program code to the host machine for operation of the integrated imaging device (if required), setting the host to a pending connection state.

S3, communicatively connecting the integrated imaging device to the paired host based on the integrated imaging device communication interface of said integrated imaging device and the host machine communication interface of said host machine;

Specifically, said integrated imaging device communication interface and said host machine communication interface are constructed on the integrated imaging device and the host machine, respectively, for accomplishing a communication connection between the integrated imaging device and the host machine to realize a bi-directional data transmission. The means of communication connection includes a wireless connection and a wired connection. Wherein said host machine communication interface is at least a portion of a host machine that has been configured with a computer, and belongs to a generic computer interface within the host machine.

S4, operating the integrated imaging device and displaying ultrasound data generated by the integrated imaging device on a user terminal of said host machine.

Specifically, when the communication connection is established, said integrated imaging device becomes an external device of the computer in the host machine. At the same time, a user terminal of the host machine becomes a terminal device of the integrated imaging device for displaying ultrasound images, displaying ultrasound-related data, controlling the operation of the integrated imaging device, managing the database, and post-processing data.

In an embodiment of the present application, all processing of the ultrasound data is accomplished by the integrated imaging device, and the processed ultrasound data is transmitted to the user terminal for display via a common interface of the host machine, and therefore, said step S4 comprises:

S41', acquiring and processing the ultrasound data through the integrated imaging device;

S42', transmitting the processed ultrasound data to the user terminal for display via the universal interface of the host machine.

Further, a method for expanding functions of an ultrasonic imaging device provided by the present application may also utilize a cloud server to analyze and process the data, and complete all or part of the data processing in the cloud. Thus, in yet another embodiment of the present application, step S4 comprises:

S41, transferring the ultrasound data obtained by the integrated imaging device to a cloud server;

S42, performing signal processing, image processing, image reconstruction, and/or multidimensional visualization on the ultrasound data on the cloud server;

S43, transmitting the processed ultrasound data to the user terminal for display.

The application is also described above with the aid of functional modules illustrating certain important functions. For the convenience of description, the boundaries of these functional constituent modules are specifically defined herein. Variations in the boundaries of these important functions are permissible when they are properly implemented. Similarly, flowchart modules are specifically defined herein to illustrate certain important functions, and for a wide range of applications, the boundaries and order of the flowchart modules may be additionally defined as long as these important functions are still realized. Changes in the boundaries and order of the functional modules and flowchart functional modules described above should still be considered to be within the scope of claim protection.

The present application may also be implemented by means of a computer program product, the program containing all the features capable of implementing the methods of the present application when installed in a computer system. A computer program in this document refers to: any expression for a set of instructions that can be written in any programming language, code or symbol, which gives the system an information processing capability to implement a specific function directly, or to implement a specific function after one or both of the following steps have been performed: a) converted into other languages, codes or symbols; and b) reproduced in a different format.

Although the present application is illustrated by specific embodiments, those skilled in the art should understand that various transformations and equivalent substitutions can be made to the present application without departing from the scope of the present application. In addition, various modifications can be made to the present application for specific situations or materials without departing from the scope of the present application. Therefore, the present application is not limited to the specific embodiments disclosed, but should include all embodiments falling within the scope of the claims of the present application.

The above is only a preferred embodiment of the present application, and is not intended to limit the present application, and any modifications, equivalent substitutions and improvements made within the spirit and principles of the present application shall be included in the scope of protection of the present application.

The invention claimed is:

1. A method for expanding functions of an ultrasonic imaging device, wherein, comprises the following steps:

- identifying and comparing functions of an integrated imaging device and a to-be-expanded ultrasonic imaging device, the to-be-expanded ultrasonic imaging device being an existing ultrasonic imaging device that has an ultrasound imaging function of its own, and the comparing determining whether a function of the integrated imaging device is supported by the to-be-expanded ultrasonic imaging device;
- on the basis of a comparison result, configuring operating parameters and modes of both the integrated imaging device and the to-be-expanded ultrasonic imaging device which serves as a host machine;
- enabling the integrated imaging device to be in communication with the host machine;
- operating the integrated imaging device and displaying ultrasound data by means of a user terminal of the host machine.

2. The method for expanding functions of an ultrasonic imaging device according to claim 1, wherein, the functions of the integrated imaging device and the to-be-expanded ultrasonic imaging device is identified based on user's inputs to the integrated imaging device, user's inputs to the host machine, and/or sensing information from at least one sensor.

3. The method for expanding functions of an ultrasonic imaging device according to claim 1, wherein, if the comparison result indicates that the function of the integrated imaging device is not compatible with the function supported by the to-be-expanded ultrasonic imaging device, the configuring comprises configuring the host machine by importing packaged executable program code to the host machine.

4. The method for expanding functions of an ultrasonic imaging device according to claim 1, wherein, the ultrasound data includes ultrasound images, videos, and measurement values that have been processed through signal and/or image processing techniques; the integrated imaging device is connected to a universal interface of the host machine.

5. The method for expanding functions of an ultrasonic imaging device according to claim 1, wherein, the operating the integrated imaging device and displaying ultrasound data comprises:

- transferring the ultrasound data obtained by the integrated imaging device to a cloud server;
- performing signal processing, image processing, image reconstruction, and/or multidimensional visualization on the ultrasound data on the cloud server;
- transmitting the processed ultrasound data to the user terminal for display.

6. The method for expanding functions of an ultrasonic imaging device according to claim 1, wherein, the operating the integrated imaging device and displaying ultrasound data comprises:

- acquiring and processing the ultrasound data through the integrated imaging device;
- transmitting the processed ultrasound data to the user terminal for display via a universal interface of the host machine.

7. A functionally expandable ultrasonic imaging system, wherein, comprises an integrated imaging device and a host machine of a to-be-expanded ultrasonic imaging device, the to-be-expanded ultrasonic imaging device being an existing ultrasonic imaging device that has an ultrasound imaging function of its own, and the host machine being a part of the to-be-expanded ultrasonic imaging device, the integrated imaging device comprises:

- an imaging device, used to scan an object under test and process corresponding ultrasound data;
- an integrated imaging device communication interface, used to establish a communication connection with the host machine, enabling bidirectional data transmission between the integrated imaging device and the host machine;
- an integrator, used to identify and compare functions of the integrated imaging device and the host machine so as to determine whether a function of the integrated imaging device is supported by the to-be-expanded ultrasonic imaging device, and on the basis of a comparison result, configure operating parameters and modes of the integrated imaging device and the host machine;

the host machine comprises:

- a user terminal, used to operate the integrated imaging device and display the ultrasound data;
- a host machine communication interface, used to establish a communication connection with the integrated imaging device, enabling bidirectional data transmission between the integrated imaging device and the host machine.

8. The functionally expandable ultrasonic imaging system according to claim 7, wherein, the host machine communication interface is a universal interface of the host machine; the ultrasound data includes ultrasound images, videos, and measurement values that have been processed through signal and/or image processing techniques.

9. The functionally expandable ultrasonic imaging system according to claim 7, wherein, the functions of the integrated imaging device and the to-be-expanded ultrasonic imaging device is identified by the integrator based on user's inputs to the integrated imaging device, user's inputs to the host machine, and/or sensing information from at least one sensor.

10. The functionally expandable ultrasonic imaging system according to claim 7, wherein, if the comparison result indicates that the function of the integrated imaging device is not compatible with the function supported by the to-be-expanded ultrasonic imaging device, packaged executable program code is imported to the host machine by the integrator to configure the host machine.

11. The functionally expandable ultrasonic imaging system according to claim 7, wherein, the integrated imaging device is used for at least one of the following applications: one-dimensional imaging, two-dimensional imaging, three-dimensional imaging, four-dimensional imaging, elastography, elasticity measurement, viscoelasticity imaging, blood flow imaging, acoustic attenuation imaging, and ultra-high-speed ultrasound imaging.

12. The functionally expandable ultrasonic imaging system according to claim 7, wherein, the communication connection between the integrated imaging device communication interface and the host machine communication interface can be either wireless or wired.

13. The functionally expandable ultrasonic imaging system according to claim 7, wherein, the integrated imaging device also includes at least one sensor that is used to perceive operational status information of the integrated imaging device, and based on the operational status information, facilitate pairing and integration between the integrated imaging device and the host machine.

14. The functionally expandable ultrasonic imaging system according to claim 7, wherein, signal processing, image processing, and image reconstruction on the images are performed by the imaging device.

15. The functionally expandable ultrasonic imaging system according to claim 7, wherein, further comprises a cloud server, used to perform at least one of the following functions: the signal processing, image processing, image reconstruction, and/or multidimensional display.

16. The functionally expandable ultrasonic imaging system according to claim 15, wherein, the cloud server is wirelessly connected to the integrated imaging device.

17. The functionally expandable ultrasonic imaging system according to claim 15, wherein, the cloud server is wirelessly connected to the host machine.

18. The functionally expandable ultrasonic imaging system according to claim 7, wherein, the integrated imaging device includes a user interface that is used to receive user's inputs and/or implement certain functions of the user terminal in the host machine.

19. The functionally expandable ultrasonic imaging system according to claim 7, wherein, the imaging device can be an ultrasonic imaging device, an optoacoustic imaging device, or a thermoacoustic imaging device.

20. The functionally expandable ultrasonic imaging system according to claim 7, wherein, the integrated imaging device further comprises a power supply unit.

* * * * *